(12) United States Patent
Christensen et al.

(10) Patent No.: US 7,727,285 B2
(45) Date of Patent: Jun. 1, 2010

(54) PROSTHETIC FOOT WITH VARIABLE MEDIAL/LATERAL STIFFNESS

(75) Inventors: Roland J. Christensen, Gunnison, UT (US); Marcus Boren, Sterling, UT (US)

(73) Assignee: Freedom Innovations, LLC, Irvine, CA (US)

( * ) Notice: Subject to any disclaimer, the term of this patent is extended or adjusted under 35 U.S.C. 154(b) by 93 days.

(21) Appl. No.: 12/011,026

(22) Filed: Jan. 22, 2008

(65) Prior Publication Data

US 2008/0188951 A1 Aug. 7, 2008

Related U.S. Application Data

(60) Provisional application No. 60/898,106, filed on Jan. 24, 2007, provisional application No. 60/901,854, filed on Feb. 16, 2007.

(51) Int. Cl.
*A61F 2/66* (2006.01)
(52) U.S. Cl. ...................................................... 623/55
(58) Field of Classification Search .............. 623/47–56
See application file for complete search history.

(56) References Cited

U.S. PATENT DOCUMENTS

| 42,799 A | 5/1864 | Shepard |
| 92,031 A | 6/1869 | Foster |
| 292,800 A | 2/1884 | Furrer |
| 497,026 A | 5/1893 | Judson |
| 1,001,641 A | 8/1911 | Harrison |
| 1,191,633 A | 5/1916 | Waggott |
| 1,289,580 A | 12/1918 | Vincenti |
| 1,779,765 A | 3/1930 | Eichhorn |
| 1,996,874 A | 8/1935 | Mascau |
| 2,036,830 A | 4/1936 | Rowley |
| 2,379,538 A | 7/1945 | Meierhofer |

(Continued)

FOREIGN PATENT DOCUMENTS

BR 9304552 7/1995

(Continued)

OTHER PUBLICATIONS www.micacorp.com/products/genesis2/, MICA Manufacturing Corporation, Genesis II Prosthetic Foot, Nov. 24, 2004, 1 page.

(Continued)

*Primary Examiner*—Thomas J Sweet
*Assistant Examiner*—Marcia Hoffman
(74) *Attorney, Agent, or Firm*—Thorpe North & Western LLP

(57) ABSTRACT

A prosthetic foot includes an elongated foot member, extending between a toe section positioned at a toe location of a natural foot and a heel section positioned at a heel location of a natural foot. The elongated foot member also extends through an elevated arch section positioned between the toe section and heel section at an approximate arch location of a natural foot. An arch block is disposed below the elongated foot member under the elevated arch section. The arch block is sized and shaped to substantially fill a space or volume under the arch section. The arch block has geometric and physical properties that facilitate medial to lateral rotation to the prosthetic foot.

23 Claims, 4 Drawing Sheets

U.S. PATENT DOCUMENTS

| | | |
|---|---|---|
| 2,443,356 A | 4/1948 | Mathis |
| 2,453,969 A | 11/1948 | Carter |
| 2,470,480 A | 5/1949 | Fogg |
| 2,570,735 A | 10/1951 | Weise |
| 2,617,115 A | 11/1952 | Ellery |
| 2,640,200 A | 6/1953 | Wisbrun |
| 2,843,853 A | 7/1958 | Mauch |
| 3,206,235 A | 9/1965 | Albinson et al. |
| 3,548,420 A | 12/1970 | Spence |
| 3,551,914 A | 1/1971 | Woodall |
| 3,754,286 A | 8/1973 | Ryan |
| 3,858,379 A | 1/1975 | Graves et al. |
| 3,871,032 A | 3/1975 | Karas |
| 3,874,004 A | 4/1975 | May |
| 3,906,552 A | 9/1975 | Weber |
| 3,920,610 A | 11/1975 | Wagner |
| 3,956,775 A | 5/1976 | Moore |
| 3,982,280 A | 9/1976 | Asbelle et al. |
| 4,089,072 A | 5/1978 | Glabiszewski |
| 4,328,594 A | 5/1982 | Campbell et al. |
| 4,442,554 A | 4/1984 | Copes |
| 4,506,395 A | 3/1985 | Haupt |
| 4,547,913 A | 10/1985 | Phillips |
| 4,606,332 A | 8/1986 | Gibson |
| 4,636,220 A | 1/1987 | Ziegelmeyer |
| 4,645,509 A | 2/1987 | Poggi et al. |
| 4,676,800 A | 6/1987 | Chen |
| 4,676,801 A | 6/1987 | Lundeen |
| 4,721,510 A | 1/1988 | Cooper et al. |
| 4,822,363 A | 4/1989 | Phillips |
| 4,865,611 A | 9/1989 | Al-Turaiki |
| 4,865,612 A | 9/1989 | Arbogast et al. |
| 4,938,775 A | 7/1990 | Morgan |
| 4,959,073 A | 9/1990 | Merlette |
| 5,019,109 A | 5/1991 | Voisin |
| 5,030,239 A | 7/1991 | Copes |
| 5,037,444 A | 8/1991 | Phillips |
| 5,062,859 A | 11/1991 | Naeder |
| 5,112,356 A | 5/1992 | Harris et al. |
| 5,116,383 A | 5/1992 | Shorter et al. |
| 5,116,384 A | 5/1992 | Wilson et al. |
| 5,156,632 A | 10/1992 | Wellershaus |
| 5,181,932 A | 1/1993 | Phillips |
| 5,181,933 A | 1/1993 | Phillips |
| 5,217,500 A | 6/1993 | Phillips |
| 5,219,365 A | 6/1993 | Sabolich |
| 5,258,039 A | 11/1993 | Goh et al. |
| 5,267,633 A | 12/1993 | Endo et al. |
| 5,290,319 A | 3/1994 | Phillips |
| 5,314,499 A | 5/1994 | Collier, Jr. |
| 5,376,133 A | 12/1994 | Gramnas |
| 5,376,139 A | 12/1994 | Pitkin |
| 5,376,141 A | 12/1994 | Phillips |
| 5,387,246 A | 2/1995 | Phillips |
| 5,405,408 A | 4/1995 | Pitkin |
| 5,425,781 A | 6/1995 | Allard et al. |
| 5,425,782 A | 6/1995 | Phillips |
| 5,443,528 A | 8/1995 | Allen |
| 5,443,529 A | 8/1995 | Phillips |
| 5,458,656 A | 10/1995 | Phillips |
| 5,464,441 A | 11/1995 | Phillips |
| 5,482,513 A | 1/1996 | Wilson |
| 5,486,209 A | 1/1996 | Phillips |
| 5,507,838 A | 4/1996 | Chen |
| 5,509,936 A | 4/1996 | Rappoport et al. |
| 5,509,937 A | 4/1996 | Allard et al. |
| 5,509,938 A | 4/1996 | Phillips |
| 5,514,185 A | 5/1996 | Phillips |
| 5,514,186 A | 5/1996 | Phillips |
| 5,549,714 A | 8/1996 | Phillips |
| 5,571,210 A | 11/1996 | Lindh |
| 5,571,213 A | 11/1996 | Allen |
| 5,593,455 A | 1/1997 | Phillips |
| 5,593,456 A | 1/1997 | Merlette |
| 5,593,457 A | 1/1997 | Phillips |
| 5,653,767 A | 8/1997 | Allen et al. |
| 5,653,768 A | 8/1997 | Kania |
| 5,695,526 A | 12/1997 | Wilson |
| 5,725,598 A | 3/1998 | Phillips |
| 5,728,175 A | 3/1998 | Rincoe |
| 5,728,176 A | 3/1998 | Phillips |
| 5,728,177 A | 3/1998 | Phillips |
| 5,746,774 A | 5/1998 | Kramer et al. |
| 5,766,265 A | 6/1998 | Phillips |
| 5,766,704 A | 6/1998 | Allen et al. |
| 5,769,896 A | 6/1998 | Rosendahl et al. |
| 5,776,205 A | 7/1998 | Phillips |
| 5,779,735 A | 7/1998 | Molino |
| 5,800,564 A | 9/1998 | Gelineau |
| 5,800,565 A | 9/1998 | Biedermann |
| 5,800,569 A | 9/1998 | Phillips |
| 5,824,112 A | 10/1998 | Phillips |
| 5,888,238 A | 3/1999 | Phillips et al. |
| 5,888,239 A * | 3/1999 | Wellershaus et al. .......... 623/55 |
| 5,893,891 A | 4/1999 | Zahedi |
| 5,899,944 A | 5/1999 | Phillips |
| 5,913,902 A | 6/1999 | Geible |
| 5,944,760 A | 8/1999 | Christensen |
| 5,957,981 A | 9/1999 | Gramnas |
| 5,976,191 A | 11/1999 | Phillips |
| 5,993,488 A | 11/1999 | Phillips |
| 6,007,582 A | 12/1999 | May |
| 6,019,795 A | 2/2000 | Phillips |
| 6,071,313 A | 6/2000 | Phillips |
| 6,077,301 A | 6/2000 | Pusch |
| 6,099,572 A | 8/2000 | Mosler et al. |
| 6,120,547 A | 9/2000 | Christensen |
| 6,165,227 A | 12/2000 | Phillips |
| 6,187,052 B1 | 2/2001 | Molino et al. |
| 6,197,068 B1 | 3/2001 | Christensen |
| 6,206,934 B1 | 3/2001 | Phillips |
| 6,228,124 B1 | 5/2001 | Slemker et al. |
| 6,241,776 B1 | 6/2001 | Christensen |
| 6,254,643 B1 | 7/2001 | Phillips |
| 6,261,324 B1 | 7/2001 | Merlette |
| 6,280,479 B1 | 8/2001 | Phillips |
| 6,290,730 B1 | 9/2001 | Pitkin et al. |
| 6,306,178 B1 | 10/2001 | Kania et al. |
| 6,402,790 B1 | 6/2002 | Celebi |
| 6,406,500 B1 | 6/2002 | Phillips |
| 6,443,993 B1 | 9/2002 | Koniuk |
| 6,443,995 B1 | 9/2002 | Townsend et al. |
| 6,514,293 B1 | 2/2003 | Jang et al. |
| 6,562,075 B2 | 5/2003 | Townsend et al. |
| 6,596,029 B1 | 7/2003 | Gramnas |
| 6,602,295 B1 | 8/2003 | Doddroe et al. |
| 6,663,673 B2 | 12/2003 | Christensen |
| 6,669,737 B2 | 12/2003 | Mosler et al. |
| 6,676,708 B1 | 1/2004 | Laghi |
| 6,740,125 B2 | 5/2004 | Mosler |
| 6,793,683 B1 | 9/2004 | Laghi |
| 6,805,717 B2 | 10/2004 | Christensen |
| 6,869,451 B1 | 3/2005 | Laghi |
| 6,875,241 B2 | 4/2005 | Christesen |
| 6,875,242 B2 | 4/2005 | Christensen |
| 6,887,279 B2 | 5/2005 | Phillips et al. |
| 6,911,052 B2 | 6/2005 | Christensen |
| 6,929,665 B2 | 8/2005 | Christensen |
| 6,966,933 B2 | 11/2005 | Christensen |
| 7,172,630 B2 | 2/2007 | Christensen |
| 7,341,603 B2 | 3/2008 | Christensen |
| 2002/0077706 A1 | 6/2002 | Phillips |
| 2002/0133237 A1 | 9/2002 | Christensen |
| 2003/0045944 A1 | 3/2003 | Mosler et al. |

| | | | | | |
|---|---|---|---|---|---|
| 2003/0191540 A1 | 10/2003 | Townsend et al. | IT | 556381 | 5/1957 |
| 2004/0068326 A1 | 4/2004 | Christensen | RU | 2033772 | 4/1995 |
| 2004/0162623 A1 | 8/2004 | Phillips | SU | 560606 | 6/1977 |
| 2005/0203640 A1 | 9/2005 | Christensen | WO | WO 94 10942 | 5/1994 |
| | | | WO | WO 02 30340 | 4/2002 |
| | | | WO | WO03/003953 | 1/2003 |

FOREIGN PATENT DOCUMENTS

| | | |
|---|---|---|
| BR | 9304225 | 11/1995 |
| DE | 295807 | 12/1916 |
| EP | 1 149 568 | 10/2001 |
| EP | 1340478 | 9/2003 |
| GB | 1191633 | 5/1970 |
| GB | 1550658 | 11/1976 |
| GB | 2244006 | 11/1991 |

OTHER PUBLICATIONS www.oandp.org/jpo/library/2000_01_009.asp, "Comparison od the seattle lite foot and genesis II prosthetic foot during walking and running." Americann Academy of Orthotists and Prosthetists, 2000, pp. 9-14, vol. 12, No. 1.

* cited by examiner

PROSTHETIC FOOT WITH VARIABLE MEDIAL/LATERAL STIFFNESS

PRIORITY CLAIM

Benefit is claimed of U.S. Provisional Patent Application Ser. No. 60/898,106, filed Jan. 24, 2007, and U.S. Provisional Patent Application Ser. No. 60/901,854, filed Feb. 16, 2007 which are herein incorporated by reference in their entirety for all purposes.

BACKGROUND OF THE INVENTION

1. Field of the Invention

The present invention relates generally to a prosthetic foot with multiaxial rotation.

2. Related Art

Many individuals have lost a limb for various reasons including war, accident, or disease. In most instances these individuals are not only able to live relatively normal lives, but physically active lives as well. Oftentimes, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited by material and imagination. Many designs have attempted to copy the anatomy of the foot or simulate its actions by replacing the bones and muscle with various mechanical simulation by replacing the entire foot with an energy storage element such as a spring. As the user steps onto the foot, the user's weight compresses the spring. As the user moves forward, the user's weight comes off the foot and the energy stored in the spring is used to propel the user forward.

Almost all of the past designs have focused on the major aspect of the prosthetic foot movement of the ankle or foot as it relates to walking or running. Few designs consider the lateral, or side to side rotation of the foot when the foot is used on varied or uneven terrain. It will be appreciated that the forefoot and heel of a natural foot rotates with a medial to lateral roll-over to accommodate variations in terrain. Most artificial feet of previous designs usually incorporate a unitary foot that is incapable of such movement.

Some designs have attempted to mimic the lateral rotation of the forefoot of a natural foot by splitting the forefoot region of the artificial foot longitudinally from the toe toward the heel, thereby effectively creating one or more "toes" on the prosthetic foot. This design is problematic, however, because the split creates at least two forefoot regions that can bend independent from one another and can result in an unnatural, out of balance feel to the user.

SUMMARY OF THE INVENTION

It has been recognized that it would be advantageous to develop a prosthetic foot with a variable stiffness arch block for providing smooth and steady multi-axial rotation laterally across the forefoot and heel regions of the foot to allow the wearer to maneuver uneven terrain. Additionally, it has been recognized that it would be advantageous to develop a prosthetic foot with a variable stiffness arch block for providing smooth and steady multi-axial rotation to assist with a natural medial to lateral roll-over of the prosthetic foot in response to uneven terrain.

In one aspect, the present invention provides for a prosthetic foot including an elongated foot member, extending between a toe section positioned at a toe location of a natural foot and a heel section positioned at a heel location of a natural foot. The elongated foot member also extends through an elevated arch section positioned between the toe section and heel section at a approximate arch location of a natural foot. An arch block is disposed below the elongated foot member under the elevated arch section. The arch block is sized and shaped to substantially fill a space or volume under the arch section. The arch block has geometric and physical properties that facilitate medial to lateral rotation to the prosthetic foot.

In another aspect, the arch block can have at least a medial portion and a lateral portion. The lateral portion can have a stiffness different than a stiffness of the medial portion. For example, the lateral portion can have a stiffness greater than a stiffness of the medial portion in order to provide a relatively softer instep and a relatively stiffer out-step. The stiffness of the medial and lateral portions can also vary between a forward and rearward section of the arch block.

Additional features and advantages of the invention will be apparent from the detailed description which follows, taken in conjunction with the accompanying drawings, which together illustrate, by way of example, features of the invention.

DETAILED DESCRIPTION

Figure 1:
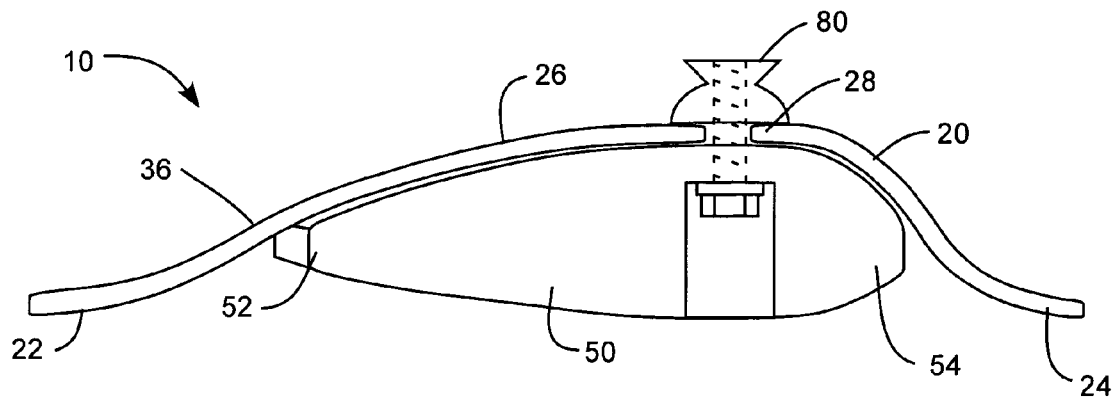
FIG. 1 is a cross section side view of a prosthetic foot with an arch block in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention relates generally to a prosthetic foot with variable medial to lateral stiffness to provide for multi-axial medial to lateral rotation. The foot can have a resilient elongated foot member extending in an arcuate shape between a toe end and a heel end with an elevated attachment section between the toe end and the heel end. The attachment section can be elevated above the toe end and heel end and can form an arch with an arch space disposed below the elongate foot member. The attachment section can be attached to the stump of an amputee. An elastic arch block can be disposed below the elongate foot member in the arch space. The arch block can have geometric and physical properties that allow medial to lateral rotation of the prosthetic foot.

Figure 2:
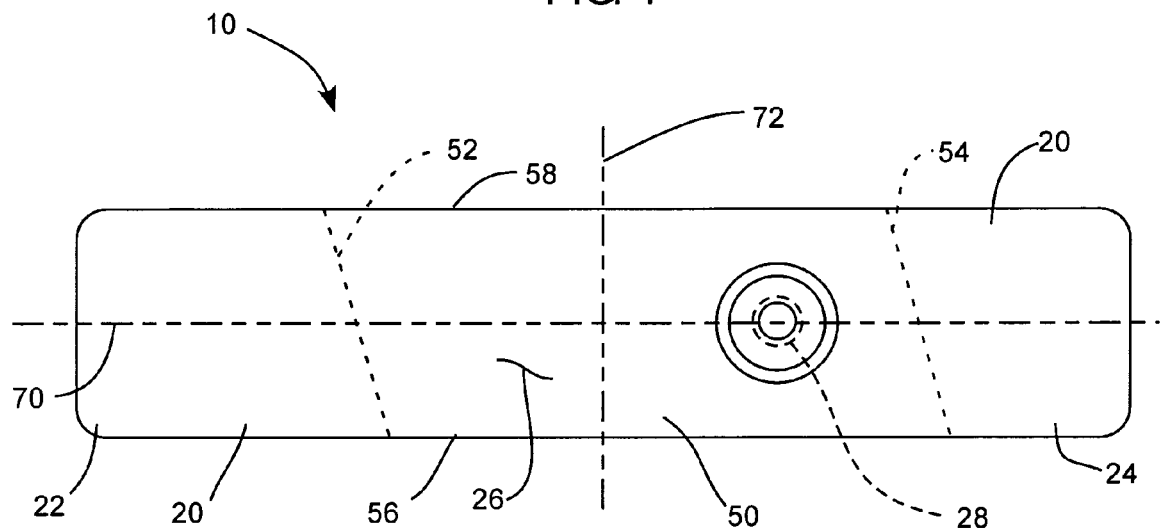
FIG. 2 is a top view of the prosthetic foot of FIG. 1.
Figure 3:
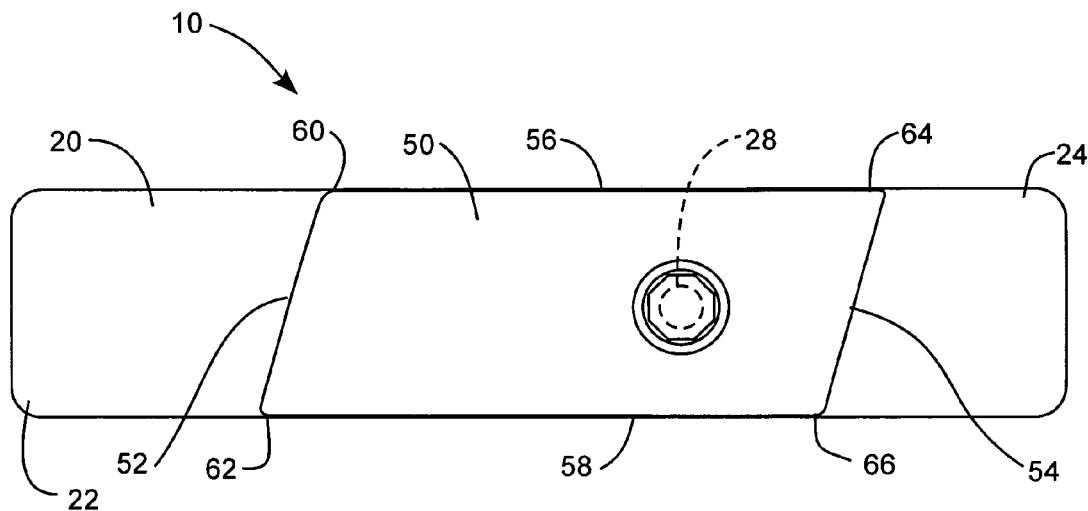
FIG. 3 is a bottom view of the prosthetic foot of FIG. 1.

As illustrated in FIGS. 1-3, a prosthetic foot, indicated generally at 10, is shown in accordance with an embodiment of the present invention. The prosthetic foot 10 can include a resilient elongate foot member 20, an elastic arch block 50 disposed under the elongate foot member, and an attachment device 80 for coupling the prosthetic foot to the stump of an amputee.

The resilient elongate foot member 20 can extend between a toe section 22 positioned at a toe location of a natural foot and a heel section 24 positioned at a heel location of a natural foot. The elongate foot member 20 can extend through an arcuate and elevated arch section 26 positioned between the toe section and heel section. The elongate foot member 20 can be formed of metal, composite, or plastic material, including for example, aluminum, Delrin®, fiberglass, carbon fiber in a resin matrix, polyurethane, polyethylene, and the like.

The elongate foot member 20 can be resilient member that can be displaced under loads applied when the user walks on the foot 10 and return to an original un-displaced shape when the loads are removed. Additionally, the elongate foot member 20 can form an energy storing leaf spring 36. In this way, the elongate foot member 20 can store energy as the leaf spring 36 is displaced when the user steps down on the foot 10 and return the stored energy to the user when the user lifts up the foot.

The elastic arch section 26 can be disposed at the approximate arch location of a natural foot. The arch section can also include an upper attachment section 28 configured to attach to the stump of an amputee. The attachment section 28 can be on the arch section in a rearward position that corresponds to the approximate location of an ankle of a natural foot. An attachment device, 80, as known in the art, can be coupled to the attachment section and can facilitate coupling of the prosthetic foot to the stump of an amputee.

The arch block 50 can be disposed below the elongated foot member 20 under the elevated arch section 26. The arch block 50 can be sized and shaped to substantially fill the space or volume under the arch section. The arch block 50 can be formed from the same materials used in the elongated foot member 20. The arch block can also be formed of fiberglass, plastic, carbon epoxy, aluminum, metal, wood, and the like. Additionally, the arch block 50 can be formed of an elastic material such that as the arch block is compressed under loads applied as the user walks on the foot, the arch block elastically returns to an original, uncompressed shape when the loads are removed.

The arch block 50 can also have geometric and physical properties that allow and facilitate medial to lateral rotation of the prosthetic foot 10 when a rotational load is applied to the foot. For example, the arch block 50 can include an angled toe end 52 and an angled heel end 54 that extend between a medial side 56 and a lateral side 58 of the arch block. The toe end 52 and heel end 54 can be angled at a non-perpendicular, oblique angle with respect to a longitudinal axis, indicated generally at 70, and at a nonparallel, oblique angle with respect to a transverse axis, indicated generally at 72, of the foot member of the prosthetic foot. Specifically, the intersection 60 of the toe end 52 with the medial side 56 can be positioned closer to the attachment section 28, arch section 26, or heel section 24 than the intersection 62 of the toe end 52 with the lateral side 58. Similarly, the intersection 64 of the heel end 54 at the medial side 56 can be positioned farther from the attachment section 28, arch section 26, or heel section 24 than the intersection 66 of the heel end 54 with the lateral side 58. In this way, the toe end 52 and heel end 54 can be angled at an oblique angle with respect to both the longitudinal axis 70 and transverse axis 72 of the foot member 20.

It will be appreciated that the toe end 52 and heel end 54 can have a variety of angles with respect to one another in order to achieve various rotational configurations of the prosthetic foot 10. Thus, in one aspect, the angle of the toe end 52 and the angle of the heel end 54 can be similar so that the toe end is parallel to the heel end, as shown in FIGS. 1-3. In another aspect, the toe end can be angled and the heel end can be perpendicular to the longitudinal axis of the prosthetic foot so as to enable rotation of the forefoot region of the prosthetic foot while limiting rotation of the heel. In yet another aspect, the toe end can be perpendicular to the longitudinal axis of the prosthetic foot and the heel end can be angled so as to enable rotation of the heel region of the prosthetic foot while limiting rotation of the forefoot region. Other angular relationships between the toe end and heel end of the arch block as known to those of skill in the art can be used to selectively increase or decrease medial to lateral roll-over of the prosthetic foot.

Figure 4:
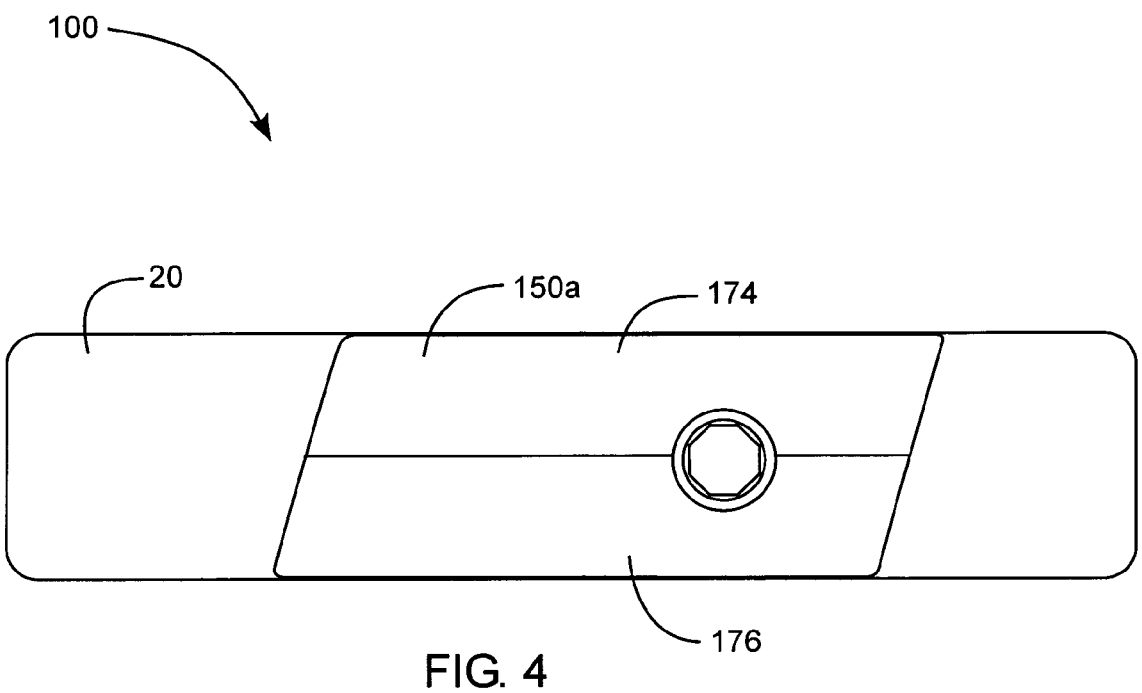
FIG. 4 is a bottom view of a prosthetic foot with an arch block having medial and lateral portions in accordance with another embodiment of the present invention.
Figure 5:
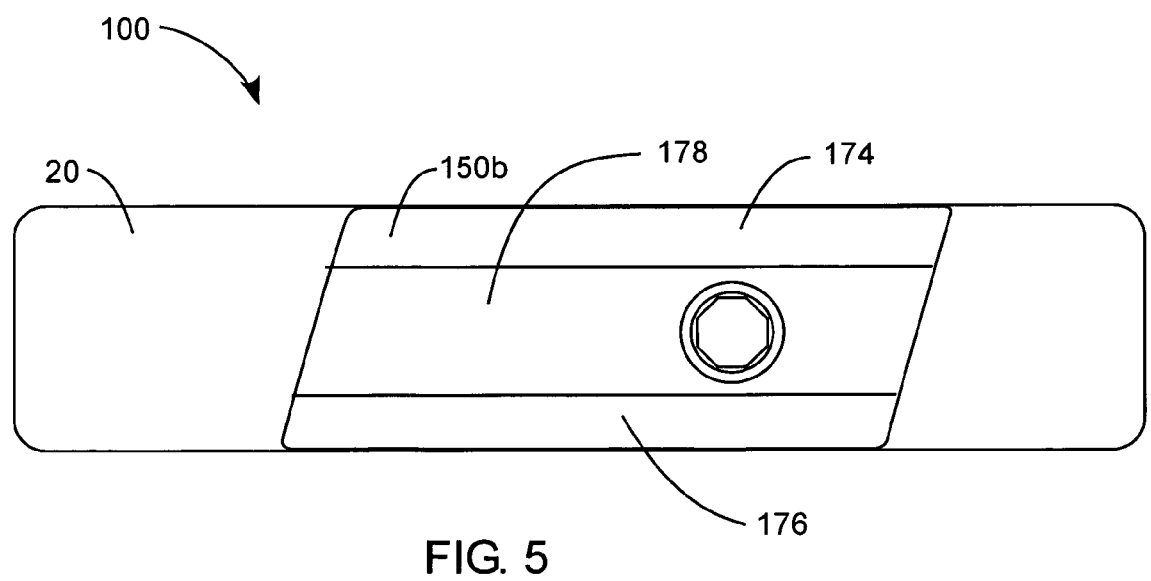
FIG. 5 is a bottom view of the prosthetic foot of FIG. 4 with another arch block having medial, intermediate, and lateral portions.

The arch block 50 can also have physical or material properties that can facilitate medial to lateral rotation of the prosthetic foot 10. For example, as shown in FIGS. 4-5, a prosthetic foot 100 is shown in accordance with another embodiment of the present invention. The prosthetic foot 100 can be similar in many respects to the prosthetic foot 10 described above and shown in FIGS. 1-3 and can include an elongate foot member 20 with an attachment device 80. Additionally, the prosthetic foot 100 can have an arch block 150*a* with at least a medial portion 174 and a lateral portion 176.

The lateral portion 174 and the medial portion 176 can each have a different stiffness so as to provide a laterally variable stiffness across the arch block 150. Thus, in one aspect, the lateral portion 176 can have a stiffness greater than the stiffness of the medial portion 174 to provide a relatively softer instep and a relatively stiffer out-step. Additionally, the arch block 150*b* can have an intermediate portion 178 between the medial and lateral portions. The intermediate portion 178 can have a greater stiffness than the medial and lateral portions.

Additionally, the arch block 150 can include a polymer material that can extend substantially the length of the medial portion 174, the lateral portion 176 and the intermediate portion 178. Accordingly, the polymer material of the intermediate portion 178 can have a greater durometer than the polymer material of the medial portion 174 and the polymer material of the lateral portion 176, and polymer material of the lateral portion can have a greater durometer than the polymer material of the medial portion. In this way, the stiffness of the polymer material can facilitate a relatively softer instep and a relatively stiffer out-step.

Advantageously, having a softer instep and stiffer out-step, as provided by the arch block 50 or 150 allows the prosthetic foot to smoothly rotate and twist about multiple longitudinal axes of the elongate foot member 20 in response to variation or uneven surfaces in the terrain. This results in a smooth and steady multi-axial rotation of the elongate foot member that can assist the wearer maintain balance and maneuver over uneven terrain by providing a natural medial to lateral roll-over of a prosthetic foot.

Figure 6:
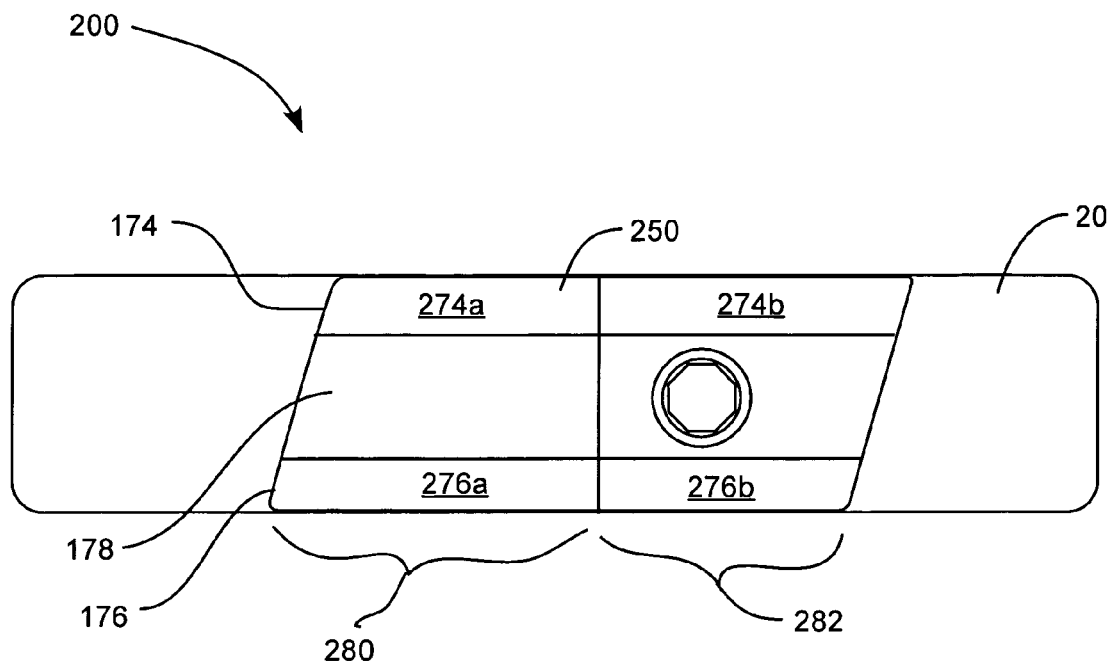
FIG. 6 is a bottom view of another prosthetic foot with an arch block having forward and rearward medial and lateral portions in accordance with another embodiment of the present invention.

As illustrated in FIG. 6, a prosthetic foot 200 is shown in accordance with another embodiment of the present invention. The prosthetic foot 200 can be similar in many respects to the prosthetic foot 10 and 100 described above and shown in FIGS. 1-5 and can include an elongate foot member 20 with an attachment device 80. Additionally, the foot 200 can include an arch block 250 having a forward section 280 and a rearward section 282.

The stiffness of the forward section 280 can be different than the stiffness of the rearward section 282. Thus, in one aspect, the forward section 280 can have a greater stiffness than the rearward section 282 to provide a softer heel-strike motion during a step. In another aspect, the forward section 280 can have a softer stiffness than the rearward section 282 so as to provide a softer toe off motion during a step.

In the case where the arch block 250 has medial, intermediate and/or lateral portions 174, 176, and 178, the stiffness of the forward section 280 and rearward section 282 can also vary with the medial to lateral portions of the arch block. Thus, in one aspect, the forward section 276a of the lateral portion 176 can have a greater stiffness than the rearward section 276b of the lateral portion, and the rearward section 274b of the medial portion can have a greater stiffness than the forward section 274a of the medial portion 174 so as to facilitate a medial to lateral rotation of the prosthetic foot 200 in a generally medial-toe to lateral-heel direction.

In another aspect, the rearward section 276b of the lateral portion 176 can have a greater stiffness than the forward section 276a of the lateral portion, and the forward section 274a of the medial portion 174 can have a greater stiffness than the rearward section 274b of the medial portion 174 so as to facilitate a medial to lateral rotation of the prosthetic foot 200 in a generally medial-heel to lateral-toe direction.

Advantageously, having a variable stiffness longitudinally along the length of the foot as well as laterally across the width of the foot, as provided by the prosthetic foot 200, allows the foot to smoothly rotate and twist about multiple longitudinal and lateral axes of the foot plate in response to variation or uneven surfaces in the terrain and also in response to dynamic movement of the foot by the user during strenuous physical activity. This smooth and steady multi-axial rotation of the foot can assist the wearer in maintaining balance and maneuvering over uneven terrain and during strenuous activity, such as running or hiking, by providing a natural medial to lateral roll-over of a prosthetic foot.

Figure 7:
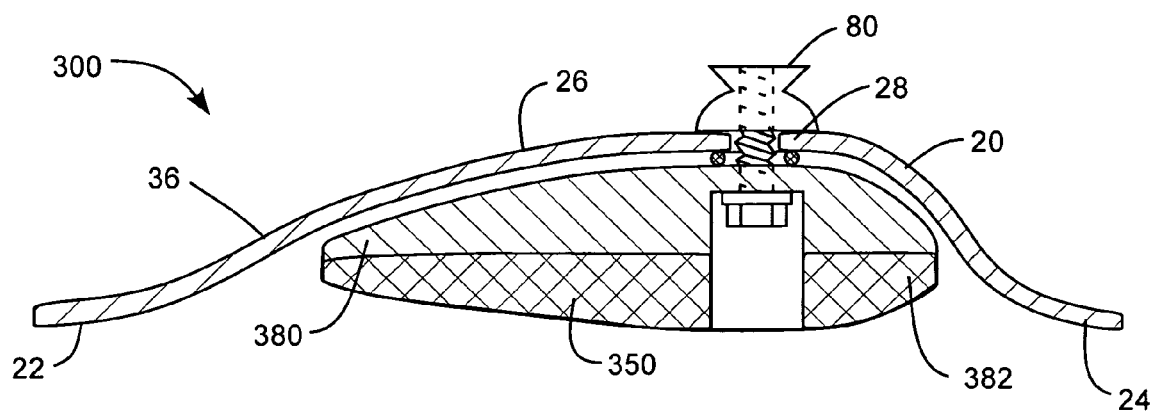
FIG. 7 is a side view of a prosthetic foot with an arch block having upper and lower portions in accordance with another embodiment of the present invention.

As illustrated in FIG. 7, a prosthetic foot 300 is shown in accordance with another embodiment of the present invention. The prosthetic foot 300 can be similar in many respects to the prosthetic feet 10, 100 and 200 described above and shown in FIGS. 1-6 and can include an elongate foot member 20 with an attachment device 80. Additionally, the foot 300 can include an arch block 350 having an upper portion 380 and a lower portion 382.

Advantageously, the upper portion 380 and the lower portion 382 can have different material properties from one another in order to facilitate multiaxial rotation of the prosthetic foot with respect to the attachment device 80 coupled to the attachment section 28. For example, the upper portion 380 can have a different stiffness or hardness than the lower section 382 so that the applied loads between the arch block 350 and the elongated foot member 20 can be at least partially absorbed in the softer upper portion.

It will be appreciated that combinations of the various prosthetic feet 10, 100, 200 and 300 described herein can be combined in accordance with the principles and concepts of the present invention. For example, the foot 300 shown in FIG. 7 having an arch block with different upper and lower sections can be combined with the foot 200 shown in FIG. 6 having an arch block with different lateral sections. Such a foot may have different sections extending both laterally across the arch block and vertically across the arch block.

Figure 8:
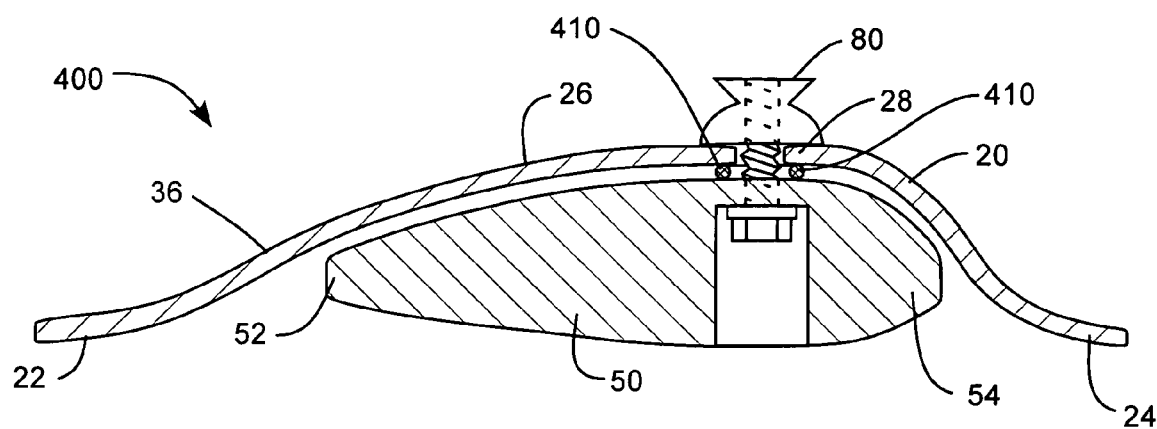
FIG. 8 is a side view of a prosthetic foot with an arch block having an elastomeric gasket disposed between an elongated foot member and an arch block in accordance with another embodiment of the present invention.

As illustrated in FIG. 8, a prosthetic foot 400 is shown in accordance with another embodiment of the present invention. The prosthetic foot 400 can be similar in many respects to the prosthetic feet 10, 100, 200 and 300 described above and shown in FIGS. 1-7 and can include an elongate foot member 20 with an attachment device 80 and an arch block 50. Additionally, the foot 400 can include an elastomeric bushing 410 disposed between the elongated foot member 20 and the arch block 50. The elastomeric bushing 410 can facilitate multiaxial rotation of the arch block 50 with respect to the elongated foot member 20, or multiaxial rotation of the elongated foot member 20 with respect to the arch block 50. In one aspect, the elastomeric bushing 410 can be a rubber o-ring. In another aspect, the elastomeric bushing 410 can be a polymeric washer. It will be appreciated that other elastomeric materials and geometric configurations can be used for the elastomeric bushing, as known in the art. For example, the elastomeric bushing 410 can be an o-ring with a uniform wall thickness, a cylindrical washer with a uniform wall thickness, a cylinder with uneven wall thickness or length from front to back or side to side, an o-ring with uneven wall thickness from front to back or side to side, and an assembly with stiffer or softer materials from front to back or side to side. Additionally, the elastomeric bushing can include the elastomeric bushing a layer of elastomeric material, a strip of elastomeric material, a grid of elastomeric material, and overlapping strips of elastomeric material as described in greater detail below.

Figure 9:
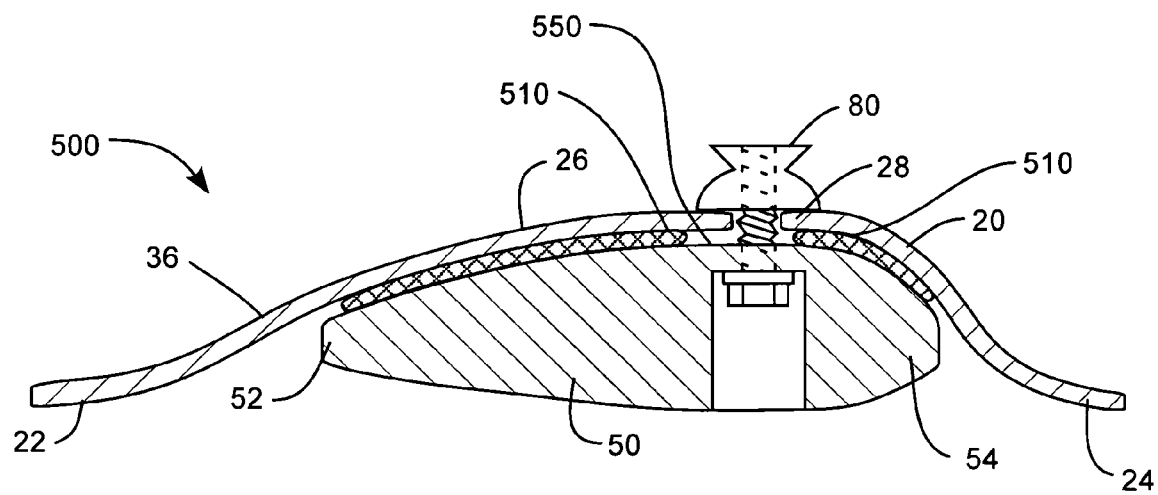
FIG. 9 is a side view of a prosthetic foot with an arch block having elastomeric strips disposed between an elongated foot member and an arch block on a top surface of the arch block in accordance with another embodiment of the present invention.

As illustrated in FIG. 9, a prosthetic foot 500 is shown in accordance with another embodiment of the present invention. The prosthetic foot 500 can be similar in many respects to the prosthetic feet described above and shown in FIGS. 1-8 and can include an elongate foot member 20 with an attachment device 80 and an arch block 50. Additionally, the foot 500 can include strips 510 of elastomeric material disposed between the elongated foot member 20 and the arch block 50. The elastomeric strips 510 can facilitate multiaxial rotation of the arch block 50 with respect to the elongated foot member 20, or multiaxial rotation of the elongated foot member 20 with respect to the arch block 50.

In one aspect, the prosthetic foot 500 can have a plurality of elastomeric strips 510 disposed laterally across a top surface 550 of the arch block 50, and each of the elastomeric strips 510 can have a different stiffness so as to facilitate lateral movement of the foot with respect to the elongate foot member 20. In another aspect, the prosthetic foot 500 can have a plurality of elastomeric strips disposed longitudinally across the top surface 550 of the arch block to facilitate longitudinal movement of the foot with respect to the elongate foot member 20. Additionally, lateral and longitudinal elastomeric strips 510 can be combined on the top surface to facilitate multiaxial rotation of the arch block 50 with respect to the elongated foot member 20.

It will be appreciated that various combinations of the geometric features and physical properties of the prosthetic foot can be made so as to configure the prosthetic foot for a particular application. For example, in one embodiment, the prosthetic foot may have an arch block only having angled toe or heel ends. As another example, the prosthetic foot may have an arch block with both angled toe and heel ends, and also with medial and lateral portions having differing stiffness. As yet another example, the prosthetic foot can include angled toe and heel ends, medial and lateral portions with variable lateral stiffness, and forward and rearward sections with variable lateral stiffness. Thus, the prosthetic foot of the present invention can advantageously be customized to accommodate a desired medial to lateral rotation or roll over.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A prosthetic foot, comprising:
   a) a resilient elongated foot member, extending between a toe section positioned at a toe location of a natural foot and a heel section positioned at a heel location of a natural foot, and extending through an elevated arch section positioned between the toe section and the heel section at an approximate arch location of a natural foot, the elevated arch section being elevated with respect to both the toe section and the heel section with the toe and heel sections disposed at the same elevation when at rest;
   b) an elastic arch block disposed below the elongated foot member under the elevated arch section, the arch block being sized and shaped to substantially fill a volume under the arch section, and configured to allow medial to lateral rotation to the prosthetic foot, the arch block also including a toe end and a heel end extending between a medial side and a lateral side of the arch block; and
   c) both the toe and heel ends of the elastic arch block being angled side to side at a nonparallel and oblique angle with respect to a transverse axis perpendicular to a longitudinal axis of the foot member.

2. A prosthetic foot in accordance with claim 1, wherein the toe end is angled such that the medial side of the toe end is positioned closer to the heel section than the lateral side of the toe end.

3. A prosthetic foot in accordance with claim 1, wherein the heel end is angled such that the medial side is positioned farther from the toe section than the lateral side of the heel end.

4. A prosthetic foot in accordance with claim 1, wherein:
   a) the toe end at the medial side is positioned closer to the heel section than the lateral side of the toe end so that the toe end is angled with respect to a transverse axis of the foot member; and
   b) the heel end at the medial side positioned farther from the toe section than the lateral side of the heel end so that the heel end is angled with respect to a transverse axis of the foot member.

5. A prosthetic foot in accordance with claim 4, wherein the toe end is substantially parallel to the heel end.

6. A prosthetic foot in accordance with claim 1, wherein the arch block has a medial portion and a lateral portion, and the lateral portion has a different stiffness than the medial portion to provide a variable stiffness laterally across the arch block.

7. A prosthetic foot in accordance with claim 6, wherein the lateral portion has a stiffness greater than a stiffness of the medial portion to provide a relatively softer instep and a relatively stiffer out-step.

8. A prosthetic foot in accordance with claim 6, further comprising:
   an intermediate portion, disposed between the medial and lateral portions, with the intermediate portion having a greater stiffness than the medial portion and the lateral portion.

9. A prosthetic foot in accordance with claim 8, wherein the arch block includes a polymer material extending substantially a length of the medial portion, the lateral portion and the intermediate portion.

10. A prosthetic foot in accordance with claim 9, wherein the polymer material of the intermediate portion has a greater stiffness than the medial portion and the lateral portion, and wherein the lateral portion has a greater stiffness than the medial portion.

11. A prosthetic foot in accordance with claim 6, wherein the lateral portion and medial portion further include a forward section and a rearward section, and a stiffness of the forward section is different than a stiffness of the rearward section.

12. A prosthetic foot in accordance with claim 11, wherein the forward section of the lateral portion has a greater stiffness than the rearward section of the lateral portion, and the rearward section of the medial portion has a greater stiffness than the forward section of the medial portion.

13. A prosthetic foot in accordance with claim 11, wherein the rearward section of the lateral portion has a greater stiffness than the forward section of the lateral portion, and the forward section of the medial portion has a greater stiffness than the rearward section of the medial portion.

14. A prosthetic foot in accordance with claim 1, wherein the elevated arch section further includes an upper attachment section configured to attach to the stump of an amputee.

15. A prosthetic foot in accordance with claim 1, wherein the arch block has an upper portion and a lower portion, the upper portion and the lower portion having different material properties to facilitate multiaxial rotation of the prosthetic foot with respect to an attachment device coupled to the attachment section.

16. A prosthetic foot in accordance with claim 1, wherein the elongate foot member further includes an energy storing leaf spring.

17. A prosthetic foot in accordance with claim 1, further comprising an elastomeric bushing disposed between the elongated foot member and the arch block and configured to facilitate multiaxial rotation of the arch block with respect to the elongated foot member.

18. A prosthetic foot in accordance with claim 17, wherein the elastomeric bushing is selected from a group consisting of an O-ring, a washer, a strip of elastomeric material, a grid of elastomeric material, overlapping strips of elastomeric material, a layer of elastomeric material, and combinations thereof.

19. A prosthetic foot, comprising:
   a) an elongated foot member, extending between a toe section positioned at a toe location of a natural foot and a heel section positioned at a heel location of a natural foot, and extending through an elevated arch section positioned between the toe section and the heel section at an approximate arch location of a natural foot, and having an upper attachment section configured to attach to the stump of an amputee; and b) an arch block disposed below the elongated foot member under the elevated arch section, the arch block being sized and shaped to substantially fill a space or volume under the arch section, and configured to allow medial to lateral rotation to the prosthetic foot, the arch block further comprising:
   i) a toe end extending between a medial side and a lateral side with the toe end at the medial side positioned closer to the attachment section than the lateral side of the toe end so that the toe end is angled side to side at a nonparallel and oblique angle with respect to a transverse axis of the foot member; and
   ii) a heel end extending between the medial side and the lateral side with the heel end at the medial side positioned farther from the attachment section than the lateral side of the heel end so that the heel end is angled side to side at a nonparallel and oblique angle with respect to the transverse axis of the foot member.

20. A prosthetic foot in accordance with claim 19, wherein the toe end between the medial and lateral sides is substantially parallel to the heel end between the medial and lateral sides.

21. A prosthetic foot in accordance with claim 19, wherein the arch block further includes:
   i) a medial portion and a lateral portion, the lateral portion and the medial portion having different stiffness to provide a laterally variable stiffness across the arch block; and
   ii) a forward section and a rearward section, the forward section and the rearward section having different stiffness to provide a longitudinally variable stiffness along the arch block.

22. A prosthetic foot, comprising:
a) an elongated foot member, extending between a toe section positioned at a toe location of a natural foot and a heel section positioned at a heel location of a natural foot, and extending through an elevated arch section positioned between the toe section and the heel section at an approximate arch location of a natural foot, and having an upper attachment section configured to attach to the stump of an amputee;
b) the toe and heel sections being disposed at the same level and an interior of the arch section being positioned above the toe and heel sections; and
c) an arch block disposed below the elongated foot member under the elevated arch section, the arch block being sized and shaped to substantially fill a space or volume under the arch section, and configured to allow medial to lateral rotation to the prosthetic foot, the arch block further comprising:
   i) a medial portion and a lateral portion, the lateral portion and the medial portion having different stiffness to provide a laterally variable stiffness across the arch block; and
   ii) a forward section and a rearward section, the forward section and the rearward section having different stiffness to provide a longitudinally variable stiffness along the arch block.
   iii) a toe end extending between a medial side and a lateral side with the toe end at the medial side positioned closer to the heel section than the lateral side of the toe end so that the toe end is angled side to side at an oblique angle with respect to a transverse axis of the foot member; and iv) a heel end extending between the medial side and the lateral side with the heel end at the medial side positioned farther from the toe section than the lateral side of the heel end so that the heel end is angled side to side at an oblique angle with respect to a transverse axis of the foot member.

23. A prosthetic foot in accordance with claim 22, wherein the toe end is substantially parallel to the heel end.

* * * * *